(12) United States Patent
Kane et al.

(10) Patent No.: US 6,556,703 B1
(45) Date of Patent: Apr. 29, 2003

(54) SCANNING ELECTRON MICROSCOPE SYSTEM AND METHOD OF MANUFACTURING AN INTEGRATED CIRCUIT

(75) Inventors: Brittin Charles Kane, Clermont, FL (US); John Martin McIntosh, Orlando, FL (US)

(73) Assignee: Agere Systems Inc., Allentown, PA (US)

( * ) Notice: Subject to any disclaimer, the term of this patent is extended or adjusted under 35 U.S.C. 154(b) by 0 days.

(21) Appl. No.: 08/957,122

(22) Filed: Oct. 24, 1997

(51) Int. Cl.⁷ .................................. G06K 9/00
(52) U.S. Cl. ................ 382/145; 382/145; 382/207; 348/87
(58) Field of Search ................ 382/144, 145, 382/147, 167, 162, 149, 217, 207, 148, 130, 209, 210; 348/80, 86, 92, 129; 364/728.03, 728.07; 250/310, 550; 356/237.1

(56) References Cited

U.S. PATENT DOCUMENTS

| | | | | |
|---|---|---|---|---|
| 4,056,716 A | * | 11/1977 | Baxter et al. ............... | 382/148 |
| 4,789,934 A | * | 12/1988 | Gundersen et al. ......... | 382/120 |
| 4,806,774 A | * | 2/1989 | Lin et al. .................... | 250/550 |
| 5,506,676 A | * | 4/1996 | Hendler et al. ........... | 356/237.1 |
| 5,523,568 A | * | 6/1996 | Ichikawa et al. ............ | 250/310 |
| 5,537,669 A | * | 7/1996 | Evans et al. ................ | 382/141 |
| 5,568,563 A | * | 10/1996 | Tanaka et al. ............... | 382/144 |
| 5,594,245 A | * | 1/1997 | Todokoro et al. ........... | 250/310 |
| 5,619,596 A | * | 4/1997 | Iwaki et al. ................. | 382/278 |
| 5,703,361 A | * | 12/1997 | Sartore ....................... | 250/310 |
| 5,754,678 A | * | 5/1998 | Hawthorne et al. ......... | 382/149 |

OTHER PUBLICATIONS

Pattern Recognition Engineering, by Nadler et al. pp. 55–57, 1993.*
Digital Image Procesing, Second Edition by William K. Pratt (pp. 15–19 and 651–653), 1991.*

* cited by examiner

*Primary Examiner*—Samir Ahmed
*Assistant Examiner*—Vikkram Bali
(74) *Attorney, Agent, or Firm*—Anthony Grillo

(57) ABSTRACT

A method and system for analyzing a substrate including the step of scanning the substrate to produce an intensity signal which represents the topography of the wafer to a first order. Other contributions to the signal intensity may be chemical composition and electrical state of the scanned features on the substrate. The scanned signal is compared and correlated to a reference signal to assess the substrate. The present invention is also directed to a method of manufacturing a wafer using the method and system and improving the manufacturing quality of product.

15 Claims, 9 Drawing Sheets

SCANNING ELECTRON MICROSCOPE SYSTEM AND METHOD OF MANUFACTURING AN INTEGRATED CIRCUIT

FIELD OF THE INVENTION

The present invention relates generally to scanning electron microscopes and, more particularly, to a scanning electronic microscope processor for analyzing semiconductor devices and a method of manufacturing an integrated circuit.

BACKGROUND OF THE INVENTION

A large amount of activity in the microelectronics industry is directed toward developing methodologies for testing wafers during the manufacturing process. Typically, scanning electron microscopes (SEM) have been used in semiconductor manufacturing processes. Although the SEM is useful for providing some information regarding a semiconductor device that is scanned, it can be difficult for an operator to detect errors by simply viewing the waveform from the SEM. Usually, an operator operates a SEM in an automatic mode to measure critical line width. The measurement is derived from the intensity waveform produced by the SEM. The SEM is not utilized to extract processing variables from the topography of the wafer. The shape of the measured object is typically not considered.

In addition, cross-sections of wafers are performed to assess the quality of a wafer. Although this process may be useful, the process is destructive and time consuming. As a result, a small number of wafers are selected for testing. An alternative approach is to perform electrical tests at the end of wafer processing to determine if deficiencies exist and assess the quality of the semiconductor devices formed on the wafer. Although deficiencies may be found, the defects are not detected until the end of wafer processing. As a result, problems in the manufacturing process or with the equipment used during manufacturing may not be detected. Numerous defective wafers may be produced before problems with the manufacturing or measurement process can be corrected.

SUMMARY OF THE INVENTION

The present invention provides a method and system for analyzing the intensity profiles of a wafer including the step of scanning the wafer to produce a scanned signal. The scanned signal is preprocessed and compared to a reference signal to assess the wafer. The present invention is also directed to a method of manufacturing a wafer using the above method and system.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice in the semiconductor industry, the various features of the drawing are not to scale. On the contrary, the dimensions of the various features are arbitrarily expanded or reduced for clarity. Included in the drawing are the following figures.

DETAILED DESCRIPTION OF THE INVENTION

Overview

The present invention is directed to a scanning electron microscope system that measures and analyzes the surface topology of a wafer during the manufacturing process. In other words, the present invention analyzes the shape of the scanned features. The surface topology is measured using a scanning electron microscope which produces intensity values in an array, an intensity profile. The intensity profile may then be processed using signal processing techniques and compared to standard waveforms from, for example, a standardized wafer which has been processed in the same manner. The standard waveforms are waveforms representing known shapes of scanned features. Differences and errors in the wafer are manifested in the measured topology and may be detected by the comparison. Errors in the measurement, i.e. focus and sharpness, by the SEM may also be determined. If the measured intensity topology can not be matched to the standard waveforms, it may be stored for further analysis. As a result, process monitoring may be improved and fatal errors in the wafers may be detected before further processing. Further, the above process may be implemented without adding additional steps to the manufacturing process because scanning electron microscopes are already used during processing.

Description of the Exemplary Embodiments

Figure 1:
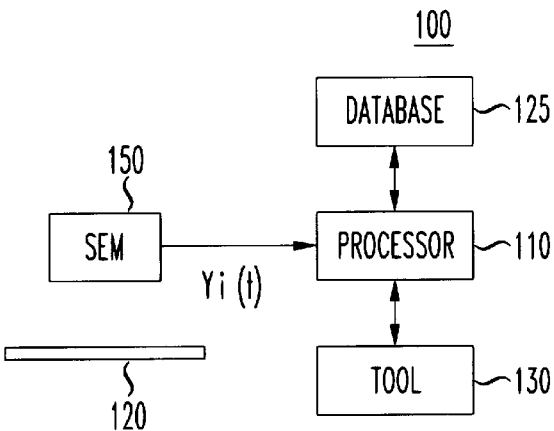
FIG. 1 is a block diagram of scanning electron microscope system 100 according to the present invention.
Figure 6:
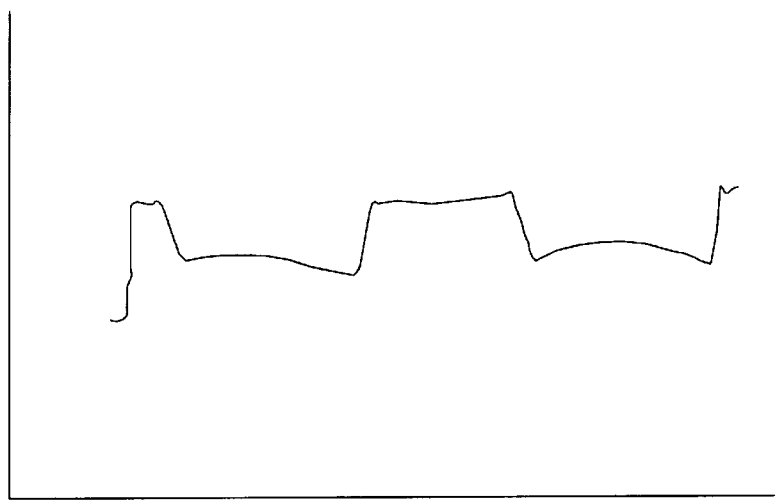
FIGS. 6–22 are graphs illustrating the operation of the scanning electron microscope system 100.

Referring now to the drawing, wherein like reference numerals refer to like elements throughout, FIG. 1 is a scanning electron microscope (SEM) system 100. The SEM system 100 includes a scanning electron microscope (SEM) 150 for scanning a wafer 120 or a substrate having a surface feature and producing a wafer waveform signal $y_r(t)$. An exemplary wafer waveform signal $y_r(t)$ for a resist line is shown in FIG. 6. The SEM 150 is, for example, Model 8820 available from Hitachi, 3100 North $1^{st}$ Street, San Jose, Calif. 95134 USA. The SEM 150 is coupled to a processor 110.

The processor 110 receives the wafer waveform signal $y_r(t)$ and detects errors and deficiencies in the wafer 120 by analyzing the wafer waveform signal $y_r(t)$. In addition, the processor 110 may detect deviations in the manufacturing process such as variations between tools. This process may be performed in-line during the manufacturing process. "In-line during the manufacturing process" means during the process of forming circuitry on the wafer 120. Consequently, process errors and degraded quality in, for example, the lithography and etching processes may be detected before manufacture of the devices is completed. Measurement errors, such as charging, may also be detected. Measurement errors can cause unnecessary reworks or scrap.

In this way, adjustments may be made in the manufacturing line to correct, for example, tool drift and tool-to-tool matching for SEMs, steppers, and etchers. This allows problems such as SEM charging, stepper out of focus, and over etch errors to be detected and corrected. Further, defective wafers may be detected and removed prior to further processing. In addition, wafer characterization may be performed to determine profile degradation across a wafer. As a result, the cost of the manufacturing process may be decreased while increasing the quality of the wafers 120 produced.

The SEM system 100 also includes a database 125 for storing reference data. The SEM system 100 may also include a tool or tools 130 that may be automatically or manually adjusted in response to the analysis performed by the SEM system 100. The components shown in FIG. 1 may be combined into one or more components and may be implemented in hardware or software. The operation of SEM system 100 is described below with reference to FIGS. 2–5. In addition, the process shown in FIGS. 2–5 is illustrated using the example shown in FIGS. 6–22.

Figure 2:
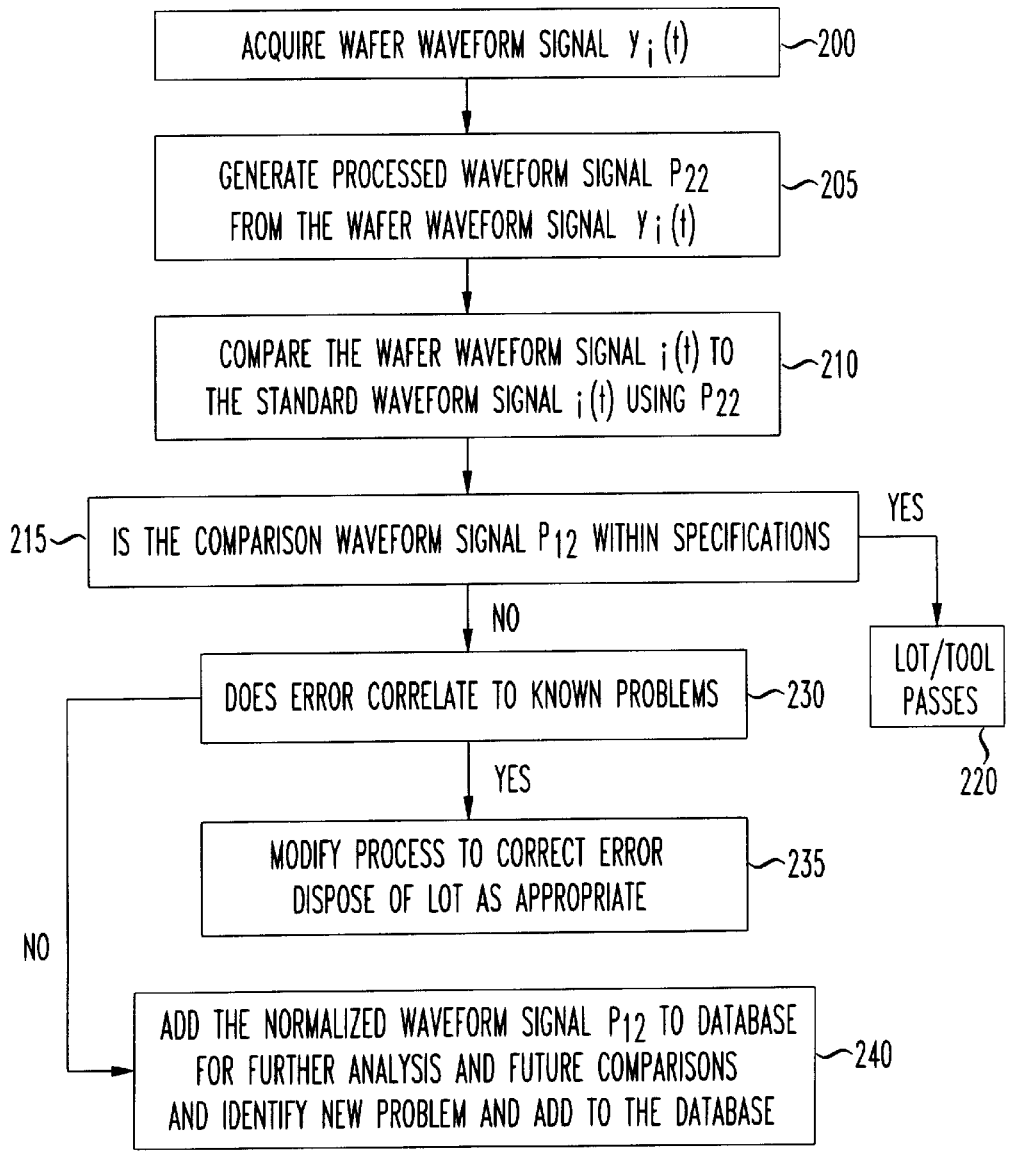
FIGS. 2–5 are flow chart diagrams for illustrating the operation of the scanning electron microscope system 100 shown in FIG. 1.
Figure 7:
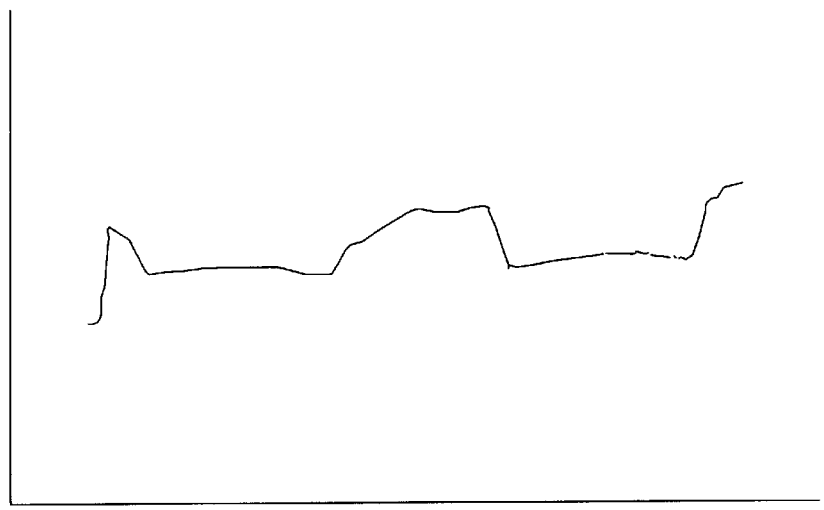
Figure 8:
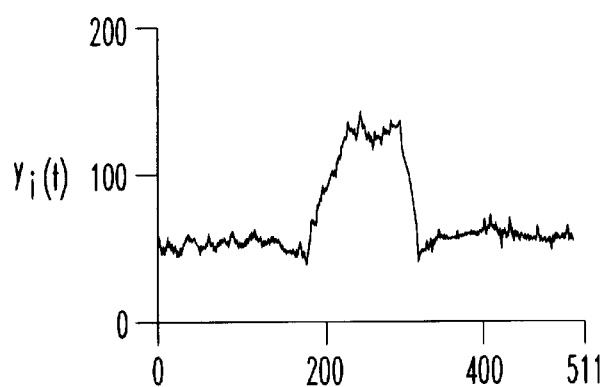

At step 200, shown in FIG. 2, the SEM 150 acquires the wafer waveform signal $y_i(t)$. An exemplary wafer waveform signal $y_i(t)$ for a charged resist line is shown in FIG. 7. FIG. 8 is a diagram corresponding to a portion of the waveform shown in FIG. 7. At step 205, the processor 110 generates a processed waveform signal $p_{22}(t)$ from the wafer waveform signal $y_i(t)$ by implementing an auto-correlation operation.

Figure 3:
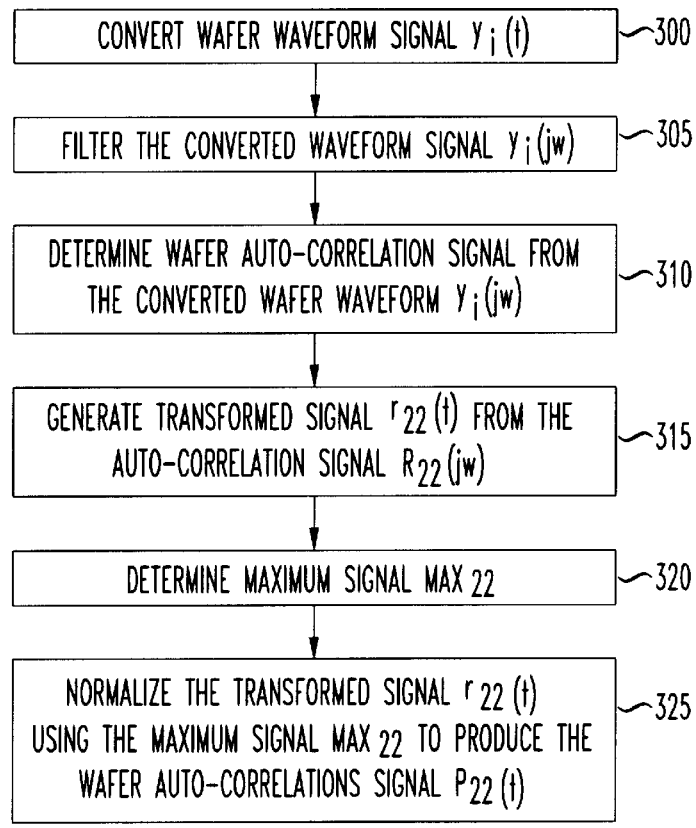

Step 205 is described in greater detail below with reference to FIG. 3. At step 300, the processor 110 processes the wafer waveform signal $y_i(t)$ using, for example, equation (1) below to produce a converted waveform signal $Y_i(jw)$.

$$F[y_i(t)]=Y_i(jw) \quad (1)$$

Figure 9:
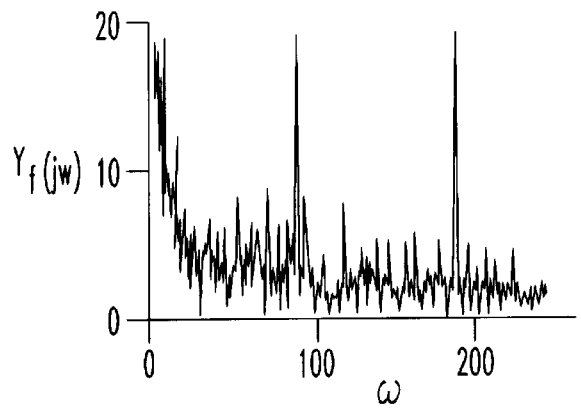

F[ ] denotes any Fourier Transform. Equation (1) implements, for example, a Fast Fourier Transform (FFT). FIG. 9 is an exemplary converted waveform $Y_i(jw)$ for the wafer waveform signal $y_i(t)$ shown in FIG. 8. At step 305 the converted waveform signal $Y_i(jw)$ is filtered using a low pass filter as is shown in equation (2) below to produce a filtered waveform signal $Y_f(jw)$.

$$\Phi[Y_i(jw)]=Y_f(jw) \quad (2)$$

Figure 10:
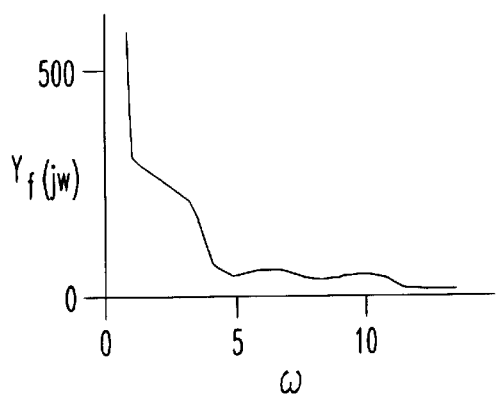

For example, the filter implemented by equation (2) may pass a quarter (¼) or less of the components of the converted waveform signal $Y_i(jw)$. The high frequency components are removed to reduce the systematic noise in the wafer waveform signal $y_i(t)$. Other filters may be used. FIG. 10 is the filtered waveform signal $Y_f(jw)$ corresponding to the converted waveform signal $Y_i(jw)$ shown in FIG. 9.

At step 310 an auto-correlation operation is performed to produce a wafer auto-correlation signal $R_{22}(jw)$ from the filtered waveform signal $Y_f(jw)$ using equation (3) below.

$$R_{22}(jw)=Y_f(jw)Y_f^*(jw) \quad (3)$$

Figure 11:
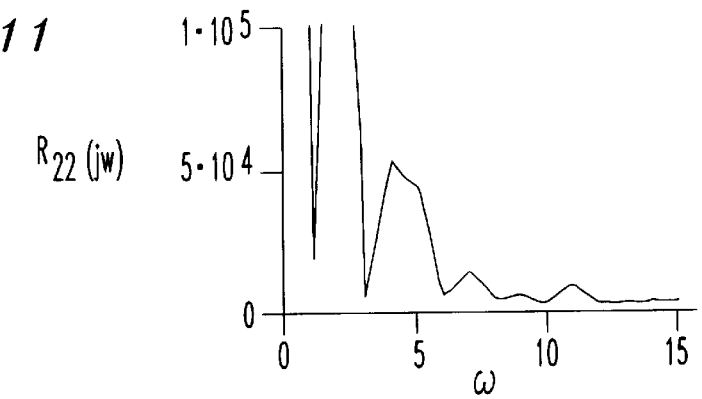

In equation (3), the "*" indicates a complex conjugate. An exemplary wafer auto-correlation signal $R_{22}(jw)$ is shown in FIG. 11. At step 315, an inverse transform is performed to produce a transformed signal $r_{22}(t)$ using equation (4) below.

$$r_{22}(t) = \frac{F^{-1}[R_{22}(jw)]}{N} \quad (4)$$

Figure 12:
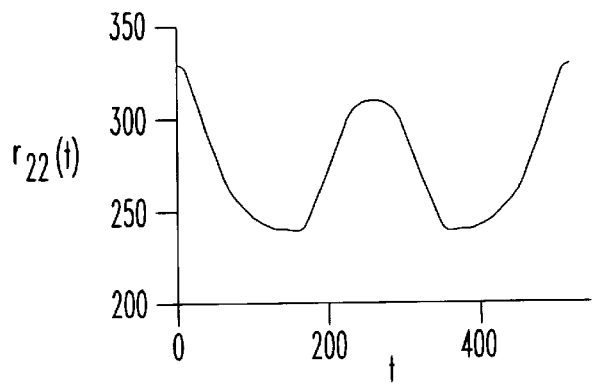

In equation (4), N is the total number of pixels that would be used for displaying the waveform or the total number of input quantities (samples). For example, an exemplary transformed signal $r_{22}(t)$ is shown in FIG. 12.

At step 320 the maximum value $MAX_{22}$ of the transformed signal $r_{22}(t)$ is determined at a phase or lag equal to zero (0) as is shown in equation (5) below.

$$MAX_{22}=r_{22}(t)(t=0) \quad (5)$$

At step 325, the transformed signal $r_{22}(t)$ is normalized according to equation (6) below to produce the auto-correlation waveform signal $p_{22}(t)$.

$$P_{22}(t) = \frac{r_{22}(t)}{Max_{22}} \quad (6)$$

Figure 13:
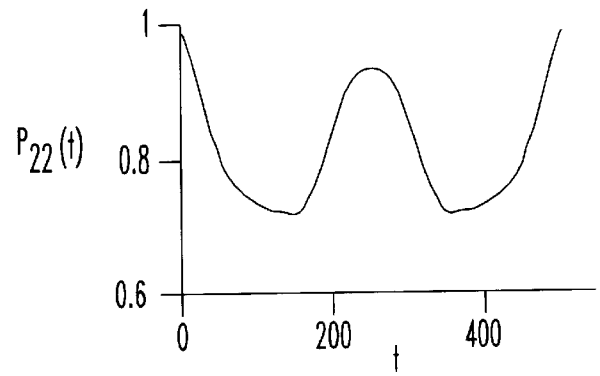

An exemplary auto-correlation signal $p_{22}(t)$ is shown in FIG. 13 where the transformed signal $r_{22}(t)$ is normalized. The result is a function of probability densities for a lag of t. This is shown for completeness, but is not necessary for further processing. The maximum value $MAX_{22}$ is, for example, 332.164.

Figure 4:
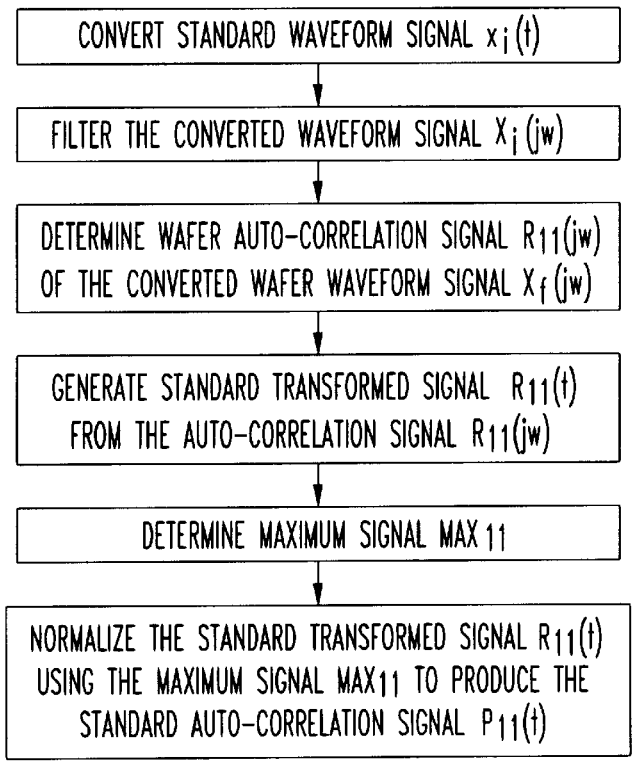
Figure 5:
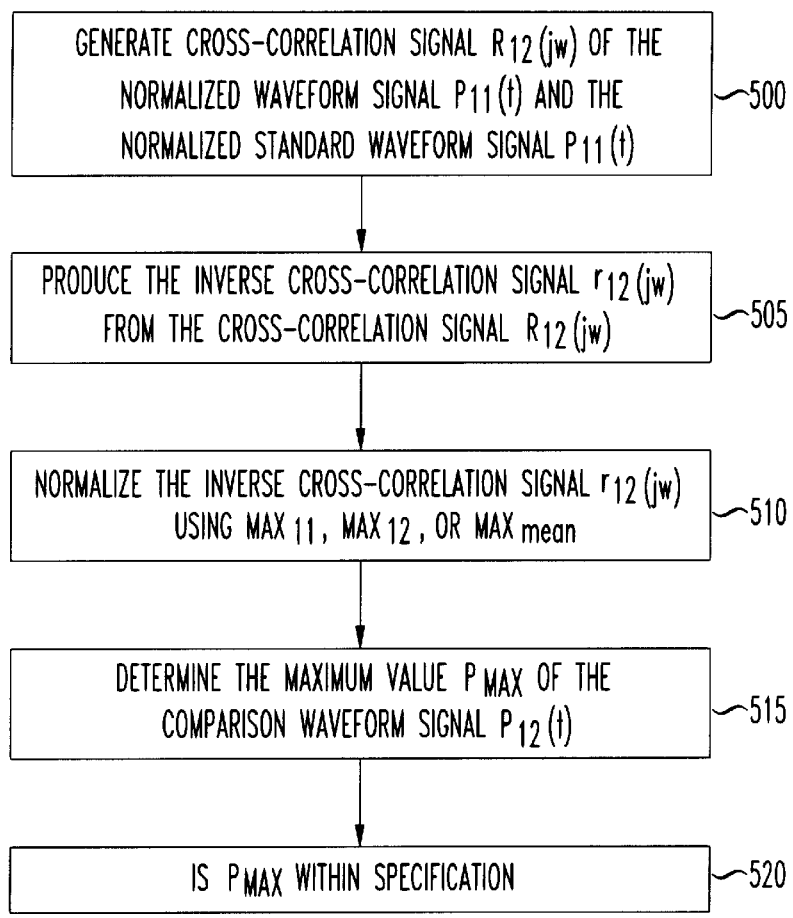

Returning to FIG. 2, at step 210 the wafer waveform signal $y_i(t)$ is compared to a standard waveform signal $x_i(t)$ using the auto-correlation signal $p_{22}(t)$. The standard waveform signal $x_i(t)$ is used as a bench mark to determine whether other wafers 120 have deficiencies and satisfy quality standards and to detect variations in the manufacturing process. The standard waveform signal $x_i(t)$ is derived from a scan of a standard wafer (not shown). The standard wafer is a wafer that satisfies the desired manufacturing criteria for producing the wafer 120. In other words, the wafer 120 is acceptable if the wafer 120 is within a specified range of the standard wafer. The process for deriving the standard auto-correlation signal $p_{11}$ is the same as the process for producing the wafer auto-correlation signal $p_{22}$ except the process is performed on a scanned signal rather than standard wafer. The process for deriving the standard auto-correlation signal $p_{11}$ is shown in FIG. 4. A description of FIG. 4 is omitted for the sake of brevity.

Figure 14:
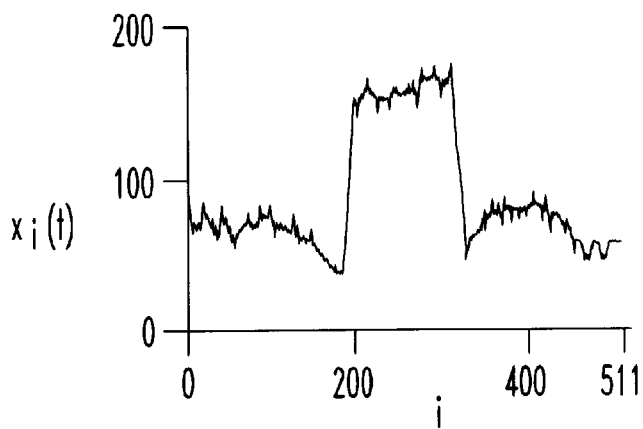
Figure 15:
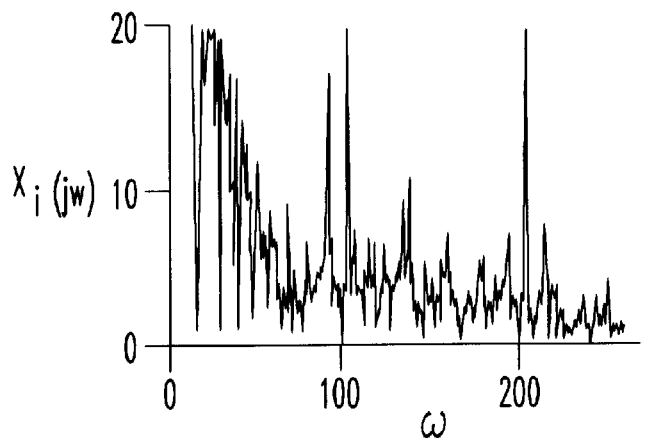
Figure 16:
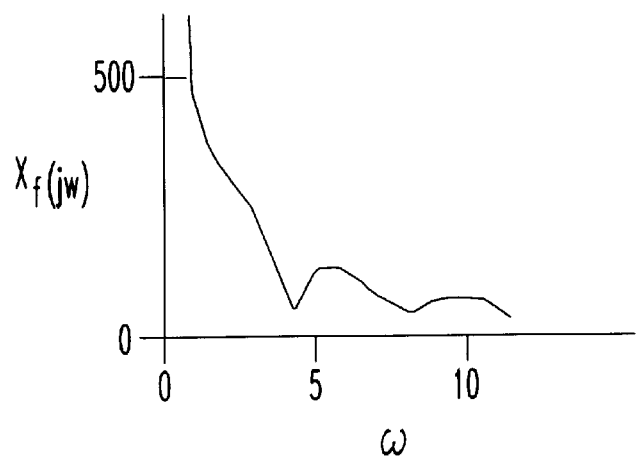
Figure 17:
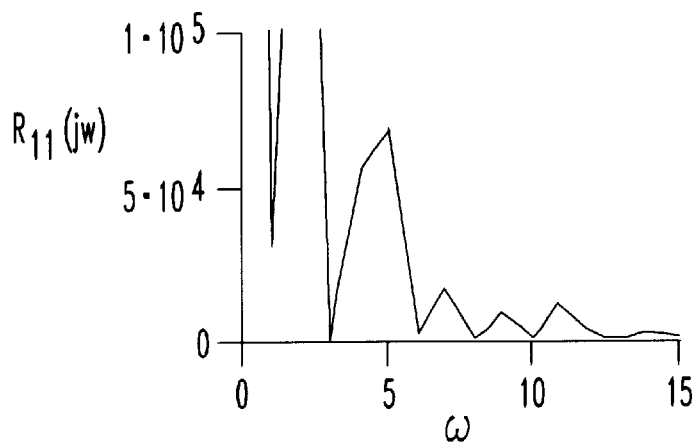
Figure 18:
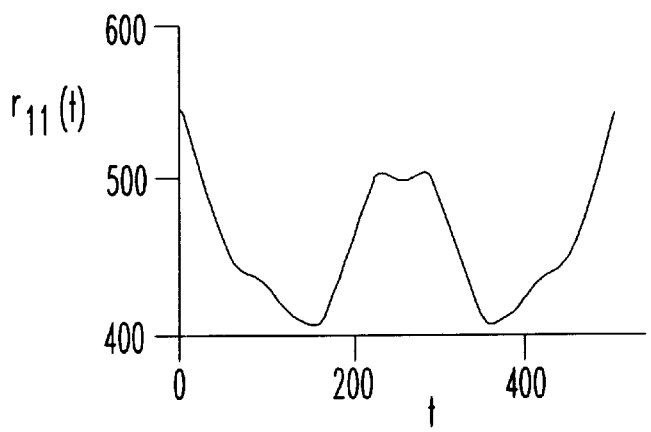
Figure 19:
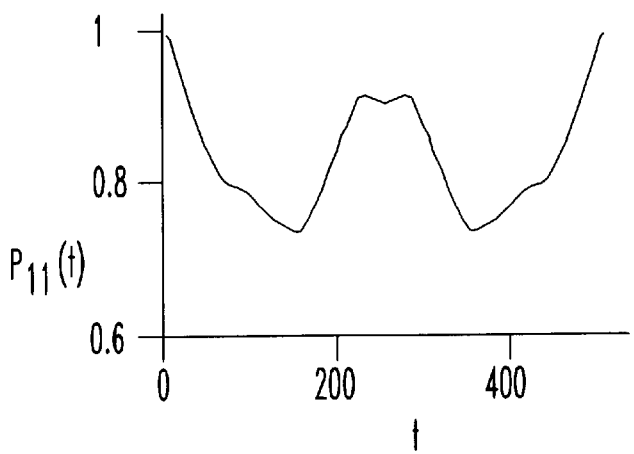

FIGS. 14–19 are exemplary waveforms corresponding to the process steps shown in FIG. 4. FIG. 14 is an exemplary standard waveform signal $x_i(t)$ for a resist line on the standard wafer. The resist line is not charged. FIG. 15 is an exemplary converted waveform $X_i(jw)$ for the wafer waveform signal $x_i(t)$ shown in FIG. 14. FIG. 16 is the filtered waveform signal $X_f(jw)$ corresponding to the converted waveform signal $X_i(jw)$ shown in FIG. 15. FIG. 17 is the wafer auto-correlation signal $R_{11}(jw)$ for the filtered waveform signal $X_f(jw)$ shown in FIG. 16. The transformed signal $r_{11}(t)$ of the auto-correlation signal $R_{11}(jw)$ is shown in FIG. 18. Finally, FIG. 19 shows the standard auto-correlation waveform signal $p_{11}(t)$ corresponding to the transformed signal $r_{11}(t)$ shown in FIG. 18. The maximum value $MAX_{11}$ used to produce the standard waveform signal $p_{11}(t)$ shown in FIG. 12 is 551.405.

Returning to FIG. 2, at step 215, the processor 110 determines whether the comparison waveform signal $p_{12}$ is within a predetermined range. Step 215 is described in greater detail in FIG. 5. At step 500, a cross-correlation signal $R_{12}(jw)$ is generated from the wafer converted waveform signal $y_f(jw)$ and the standard converted waveform signal $x_f(jw)$, calculated in earlier steps, using equation (6) below.

$$R_{12}=X_f(jw)Y_f^*(jw) \quad (6)$$

Figure 20:
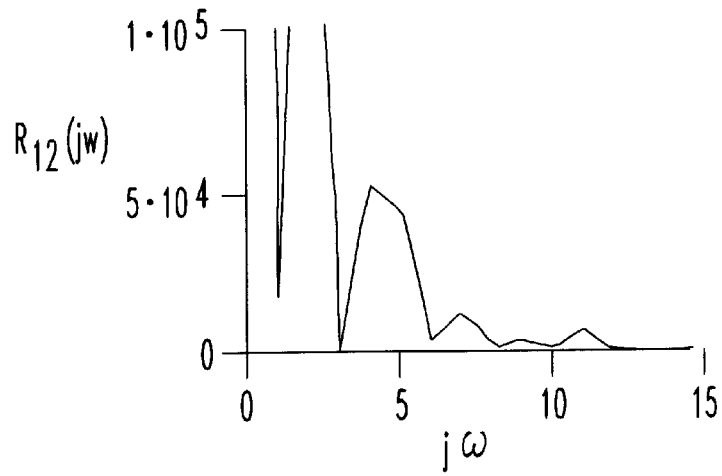

"*" indicates the complex conjugate. FIG. 20 is an exemplary cross-correlation signal $R_{12}(jw)$ of the processed waveform signal $p_{22}$ and the standard waveform signal $p_{11}$.

At step 505, the cross-correlation signal $R_{12}(jw)$ is converted to the time domain using equation (7) below to produce the unnormalized cross-correlation signal $r_{12}(t)$.

$$r_{12}(t) = \frac{F^{-1}[R_{12}(jw)]}{N} \quad (7)$$

Figure 21:
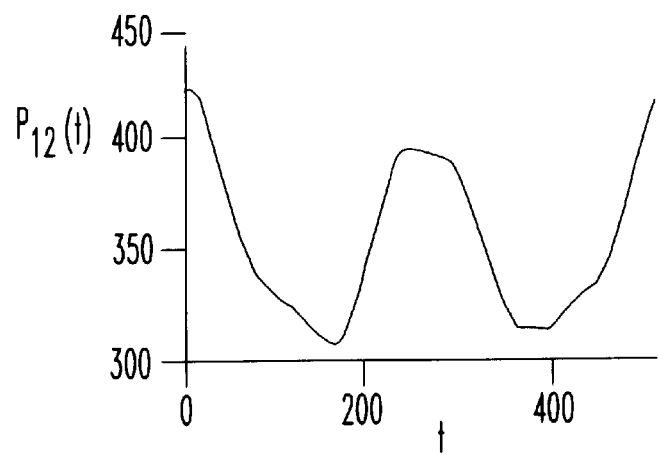

N is the same value for both signals. FIG. 21 is the unnormalized cross-correlation signal $r_{12}(t)$ corresponding to the cross-correlation signal $R_{12}(jw)$ shown in FIG. 20.

At step 510, the unnormalized cross-correlation signal $r_{12}(t)$ is normalized according to equation (8) below.

$$p_{12}(t) = \frac{r_{12}(t)}{\text{Max}_{func}} \quad (8)$$

The value $\text{Max}_{func}$ is defined in equation (9) below.

$$\text{Max}_{func} = \begin{cases} \text{Max}_{11} & \text{if Max}_{22} < \text{Max}_{11} \text{ and to compare shape and amplitude} \\ \text{Max}_{22} & \text{if Max}_{11} < \text{Max}_{22} \text{ and to compare shape and amplitude} \\ \text{or} & \\ \sqrt{\text{Max}_{22} \cdot \text{Max}_{11}} & \text{if only to compare shape} \end{cases} \quad (9)$$

Figure 22:
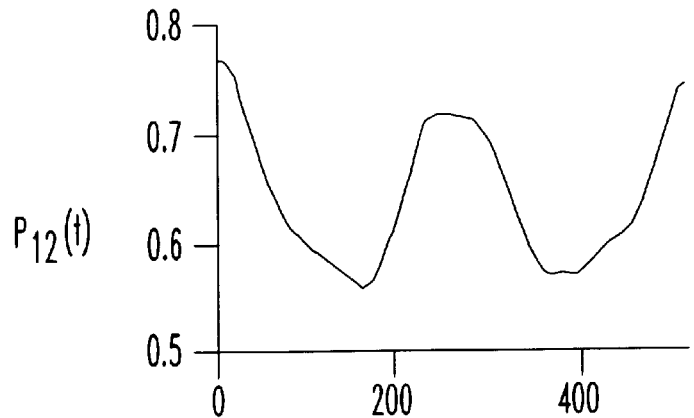

FIG. 22 shows the normalized signal $p_{12}(t)$ normalized using a $\text{Max}_{func}$ of 551.405 ($\text{Max}_{11}$). Amplitude is not considered in this case. The shape of the waveforms are only compared if there are scaling errors present, such as those caused by a degradation in the SEM 150 or when the SEM 150 is not matched to the SEM that measured the standardized wafer. At step 515, the maximum value $p_{max}$ of the comparison waveform signal $p_{12}(t)$ is determined. The maximum value $p_{max}$ for the normalized signal $p_{12}(t)$ shown in FIG. 22 is 0.767. Phase errors (picture offsets) which may occur in the SEM 150 are eliminated. As a result, the wafer waveform signal $y_t(t)$ may later be compared to a standard waveform signal $x_t(t)$ without this possible source of error.

At step 520, the processor 110 determines whether the comparison waveform signal $p_{12}(t)$ is within specification. For example, if the absolute value of the maximum value $p_{max}$ is greater than 0.9 and less than 1 ($0.90 < |p_{max}| < 1$), the wafer 120 is considered acceptable. In a production line arrangement, one or more wafers 120 may be tested to determine if an entire lot is acceptable. Otherwise, the lot may be rejected. Typically, acceptable wafers 120 have been found to have a maximum value $p_{max}$ between 0.95 and 1 ($0.95 < |p_{max}| < 1$).

Returning to FIG. 2, at step 220, the lot or tools 130 are indicated as passing if the maximum value $p_{max}$ is within the specified range. Otherwise, at step 230, the wafer waveform signal $y_t(t)$ is compared to data stored in database 125 using the same methods described earlier to determine what error has occurred and how the error may be corrected. The database 125 includes data and/or instructions for modifying the production process to eliminate the errors. At step 235, the processor 110 provides instructions to the tools 130, equipment, etc. using the data from the database 125 to correct the errors. In addition, the lot of wafers is disposed of is appropriate. Alternatively, the information may be provided to an operator via a user interface (not shown). The operator makes adjustments to the manufacturing process or measurement in response to the information.

At step 240, if there is no corresponding instructions for correcting the error, the error and the associated data are stored in the database 125 for future analysis and comparison. For example, the wafer waveform signal $y_t(t)$, the comparison waveform signal $p_{12}$, and/or any of the other signals produced or used during the analysis of the wafer 120 may be stored.

Although the above exemplary embodiment utilized a one dimensional waveform, a multi-dimensional process may be used or multiple waveforms may be compared. In addition, regions of the intensity topology may be averaged, summed, or in general signal processed, and compared. Further, the orientation of a feature may be analyzed. In this case, the wafer may be rejected if the feature does not have the proper orientation. The particular comparison that is chosen is dependent upon the particular feature to be analyzed.

Figure 23:
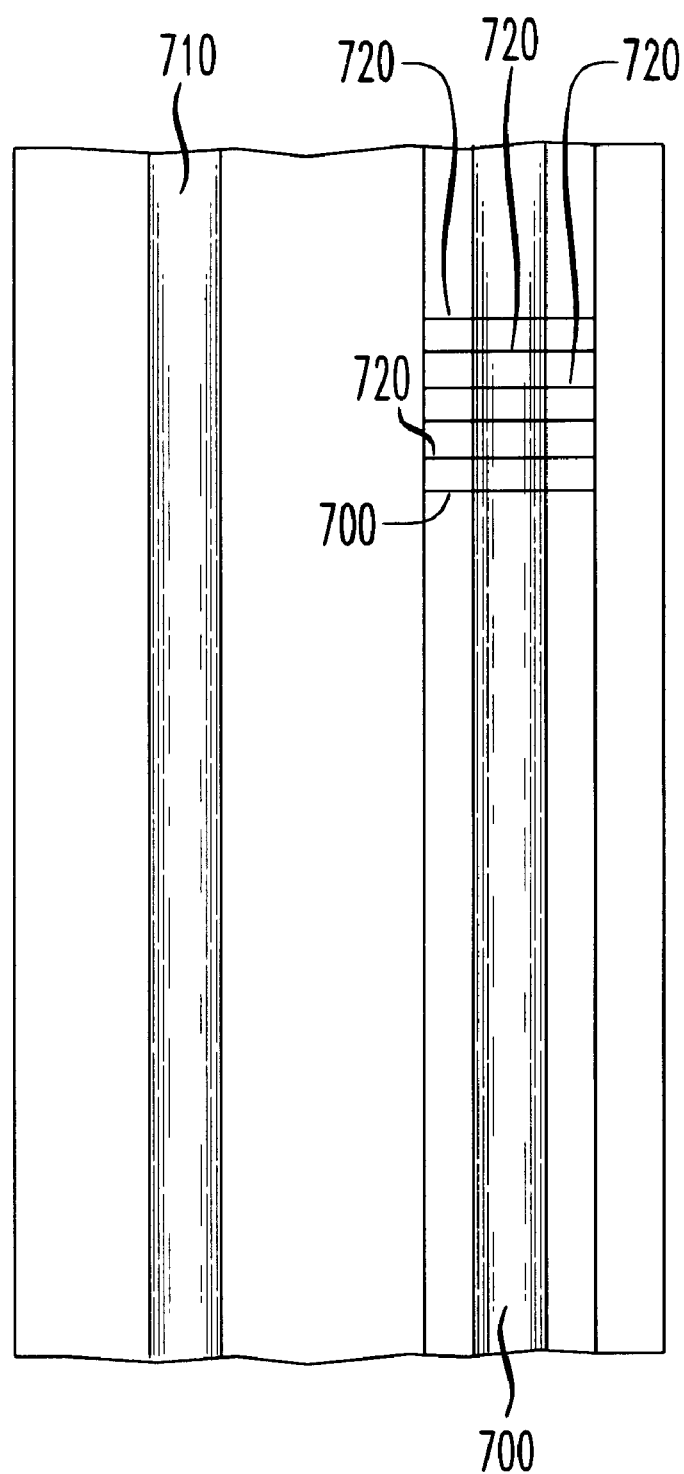
FIG. 23 is a SEM picture of a metal line on a wafer illustrating an alternative embodiment.

For example, consider FIG. 23 which is a picture of a metal line 710 formed on a substrate. One process for determining the roughness of the edge 700 of the line 710 is to compare multiple average intensities in the y-direction. An average intensity is derived by averaging intensity values of a segment 720 extending in the x-direction. If the edge 700 varies, i.e. has bulges or inflections, the average intensity varies. Variations in the edge 700 may be detected and compared to an expected or standard edge profile. The average intensities may be considered to form a waveform signal $y_t(t)$ extending in the y-direction. This waveform signal $y_t(t)$ may be processed using the process shown in FIG. 2.

The above invention is not limited to comparing the intensity profile in the x or y-directions or in straight lines. The selected comparison may include comparisons which traverse the wafer in a manner suitable to assess the particular feature. For example, the pattern may be selected to correspond to the edge of a feature which is not solely oriented in the x and y-directions.

Although the invention has been described with reference to exemplary embodiments, it is not limited to those embodiments. Rather, the appended claims should be construed to include other variants and embodiments of the invention which may be made by those skilled in the art without departing from the true spirit and scope of the present invention.

What is claimed:

1. A method for analyzing a substrate having a raised surface feature, the method comprising the steps of:
   (a) scanning the substrate to produce an intensity signal;
   (b) processing the intensity signal using an auto-correlation operation to produce a processed signal and converting the processed signal to the frequency domain, wherein the auto-correlation operation produces a wafer auto-correlation signal from a filtered waveform signal;
   (c) providing a reference signal; and
   (d) comparing the processed signal to the reference signal.

2. The method of claim 1 wherein step (a) further comprises the step of scanning the substrate using a scanning electron microscope.

3. The method of claim 1 wherein step (d) further comprises the step of cross-correlating the reference signal and the processed signal to produce an assessment value.

4. The method of claim 3 wherein step (d) further comprises the step of determining that the substrate is acceptable if the assessment value is greater than 0.9.

5. The method of claim 3 wherein step (d) further comprises the step of determining that the substrate is acceptable if the assessment value is greater than 0.95.

6. The method of claim 1 further comprising the step of adjusting a tool in response to step (d).

7. A method of manufacturing an integrated circuit comprising the steps of:
   (a) providing a wafer with at least one surface feature;

(b) scanning the wafer to produce an intensity signal representing the surface feature;

(c) processing the intensity signal using an auto-correlation operation to produce a processed signal and converting the processed signal to the frequency domain, wherein the auto-correlation operation produces a wafer auto-correlation signal from a filtered waveform signal;

(d) providing a reference signal; and (e) comparing the scanned signal to a reference signal.

8. The method of claim 7 further comprising the step of rejecting the wafer or measurement in response to step (e).

9. The method of claim 7 wherein the reference signal represents a standardized surface feature that corresponds to the at least one surface feature.

10. The method of claim 7 wherein step (b) further comprises the step of scanning the wafer using a scanning electron microscope.

11. The method of claim 7 wherein step (e) further comprises the step of cross-correlating the reference signal and the intensity signal to produce an assessment value.

12. The method of claim 11 wherein step (e) further comprises the step of determining that the wafer is acceptable if the assessment value is greater than 0.9.

13. The method of claim 11 wherein step (e) further comprises the step of determining that the wafer is acceptable if the assessment value is greater than 0.95.

14. The method of claim 7 wherein (d) further comprises the step of assessing only one surface feature.

15. A substrate analyzing system for analyzing a substrate having a surface feature, the substrate analyzing system comprising:

a scanning electron microscope for producing an intensity signal of the substrate;

auto-correlation means for implementing an auto-correlation operation to produce an auto-correlation signal from the intensity signal, wherein the auto-correlation operation produces a wafer auto-correlation signal from a filtered waveform signal;

converter means for converting the auto-correlation signal into the frequency domain;

cross-correlation means for generating a cross-correlation signal of the auto-correlation signal and a reference signal to produce a cross-correlation signal; and means for evaluating the substrate in response to the cross-correlation signal.

* * * * *